US011446453B2

(12) United States Patent
Graine et al.

(10) Patent No.: US 11,446,453 B2
(45) Date of Patent: Sep. 20, 2022

(54) ASSEMBLY FOR NASAL DISPENSING OF FLUID PRODUCT

(71) Applicant: APTAR FRANCE SAS, Le Neubourg (FR)

(72) Inventors: Lila Graine, Beynes (FR); Eric Piazzoni, Saint Cyr la Campagne (FR); Pierre Boivin, Saint Etienne du Vauvray (FR)

(73) Assignee: APTAR FRANCE SAS, Le Neubourg (FR)

( * ) Notice: Subject to any disclaimer, the term of this patent is extended or adjusted under 35 U.S.C. 154(b) by 476 days.

(21) Appl. No.: 16/469,703

(22) PCT Filed: Dec. 14, 2017

(86) PCT No.: PCT/FR2017/053588
§ 371 (c)(1),
(2) Date: Jun. 14, 2019

(87) PCT Pub. No.: WO2018/109409
PCT Pub. Date: Jun. 21, 2018

(65) Prior Publication Data
US 2020/0078543 A1    Mar. 12, 2020

(30) Foreign Application Priority Data

Dec. 15, 2016 (FR) ...................................... 1662561

(51) Int. Cl.
*A61M 15/08* (2006.01)
*A61M 11/00* (2006.01)
(Continued)

(52) U.S. Cl.
CPC .......... *A61M 15/08* (2013.01); *A61M 11/007* (2014.02); *A61M 11/06* (2013.01);
(Continued)

(58) Field of Classification Search
CPC ........... A61M 15/08–085; A61M 11/006–007; A61M 11/06; A61M 15/0045;
(Continued)

(56) References Cited

U.S. PATENT DOCUMENTS 1,155,608 A   10/1915 Nieschang
4,732,147 A *  3/1988 Fuller .................. A61M 25/02
                                              128/207.17
(Continued)

FOREIGN PATENT DOCUMENTS

DE    20 2015 006 433 U1    10/2015

OTHER PUBLICATIONS

International Search Report for PCT/FR2017/053588 dated Mar. 27, 2018 (PCT?/SA/210).
(Continued)

*Primary Examiner* — Elliot S Ruddie
(74) *Attorney, Agent, or Firm* — Sughrue Mion, PLLC

(57) ABSTRACT

A dispenser assembly comprising a nasal fluid dispenser device having a reservoir forming body (10) containing fluid or that supports such a reservoir in stationary manner, a dispenser head (20) being assembled on said body (10), said dispenser head (20) being provided with a dispenser orifice (21), said assembly further comprising a positioner member (40) that co-operates with said nasal dispenser device, said positioner member (40) including at least a first facial bearing zone (42) that, during actuation, co-operates with the forehead or the bridge of the user's nose, said dispenser head (20) being movable axially relative to said body (10), said positioner member (40) including at least one hollow sleeve (41) in which said dispenser head (20) is inserted in clamping manner, said positioner member (40) including a second facial bearing zone (46) that is adapted to co-operate with the user's top lip.

17 Claims, 4 Drawing Sheets

(51) Int. Cl.
*A61M 11/06* (2006.01)
*A61M 15/00* (2006.01)
*B05B 11/02* (2006.01)

(52) U.S. Cl.
CPC . *A61M 15/0091* (2013.01); *A61M 2210/0618* (2013.01); *B05B 11/02* (2013.01)

(58) Field of Classification Search
CPC ...... A61M 15/0091; A61M 2210/0618; B05B 11/02–048; A61F 9/0026
USPC ........ 128/20, 2 R, 198, 200, 200.14, 200.18, 128/200.21, 200.22, 200.23, 203.18, 128/203.22, 206, 207, 207.18; 600/303
See application file for complete search history.

(56) References Cited

U.S. PATENT DOCUMENTS

| | | | |
|---|---|---|---|
| 9,486,381 B2 * | 11/2016 | Juto | ................ A61H 23/02 |
| 2011/0132354 A1 | 6/2011 | Flickinger et al. | |
| 2014/0323931 A1 * | 10/2014 | Avni | ................ A61M 15/0085 |
| | | | 601/46 |
| 2017/0065780 A1 | 3/2017 | Zisser | |

OTHER PUBLICATIONS

International Preliminary Report on Patentability with translation of Written Opinion dated Jun. 18, 2019, in counterpart international Application No. PCT/FR2017/053588.

* cited by examiner

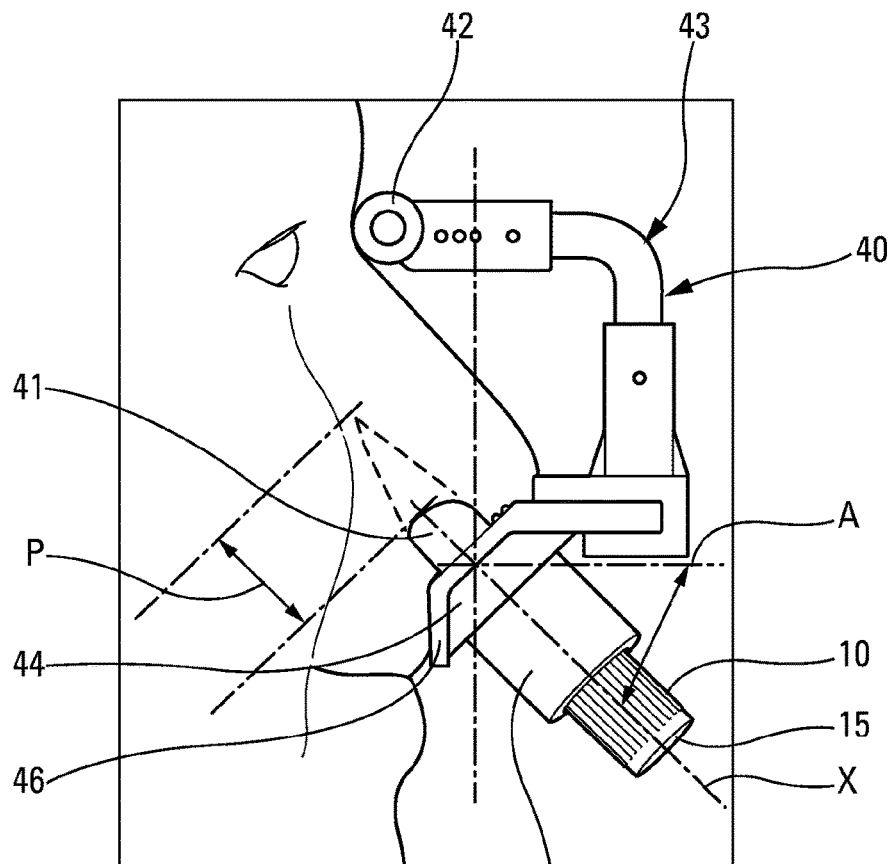
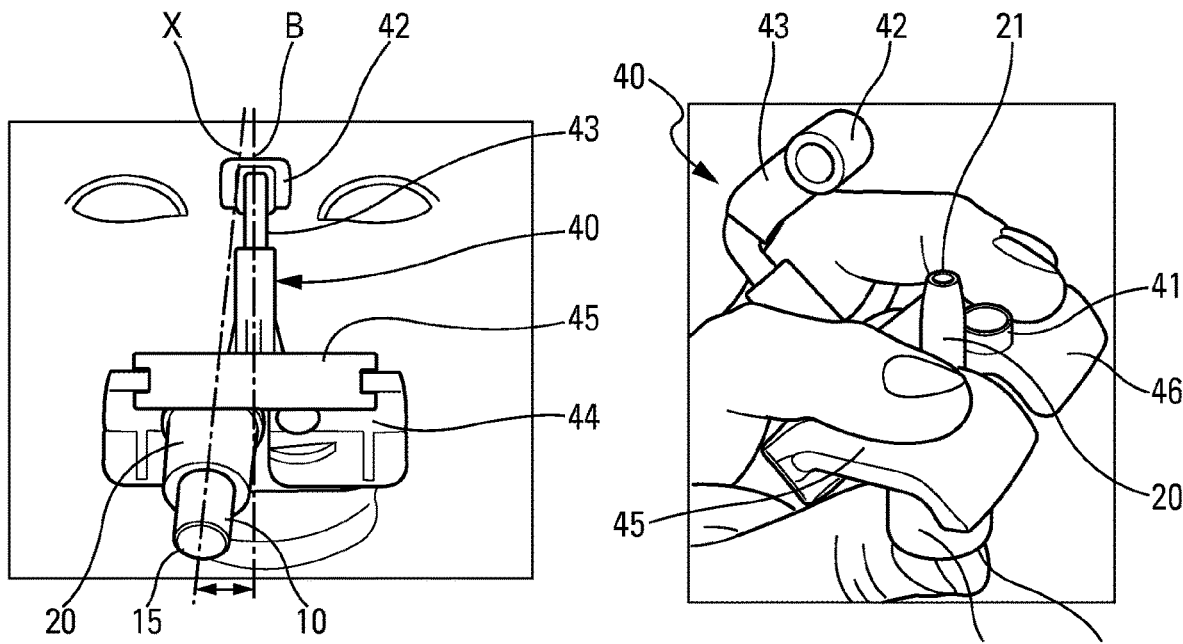
Fig. 1
Fig. 2
Fig. 3

ASSEMBLY FOR NASAL DISPENSING OF FLUID PRODUCT

CROSS REFERENCE TO RELATED APPLICATIONS

This application is a National Stage of International Application No. PCT/FR2017/053588 filed Dec. 14, 2017, claiming priority based on French Patent Application No. 1662561, filed Dec. 15, 2016.

The present invention relates to a dispenser assembly including a nasal fluid dispenser device.

Nasal dispenser devices are well known. They generally comprise a reservoir containing one or more doses of fluid, and a dispenser head that is movable relative to said reservoir so as to dispense the fluid, in particular via a pump, a metering valve, or a piston that slides in said reservoir. When the user wishes to use the device, the user inserts the dispenser head into the nostril and actuates the device so as to dispense a dose of fluid, generally in the form of spray.

A drawback with prior-art devices relates to the effectiveness of the dose that is dispensed in the nostril, in particular when the purpose of the dispensed fluid is to act on the brain. Specifically, only a tiny portion of the dose generally reaches the target zone for this type of treatment, namely the olfactory zone including the ethmoid sinuses, in particular because of the orientation of the administering device in the nostril, which varies from one patient to another. Unfortunately, it appears that this orientation determines whether targeting of the target zone is successful, in particular for a compact spray that is used to obtain the maximum deposition in the target zone.

Document U.S. Pat. No. 1,155,608 describes a nasal inhaler device.

An object of the present invention is to provide a nasal dispenser assembly that does not have the above-mentioned drawbacks.

In particular, an object of the present invention is to provide a nasal dispenser assembly that makes it possible to control the orientation of the device in the nostril, whatever the morphology of the patient.

Another object of the present invention is to provide a nasal dispenser assembly that improves the percentage of active fluid that is deposited on the olfactory zone and/or on the ethmoid sinuses.

Another object of the present invention is to provide a nasal dispenser assembly that is simple and inexpensive to manufacture and to assemble.

The present invention thus provides a dispenser assembly comprising a nasal fluid dispenser device having a reservoir forming body containing fluid or that supports such a reservoir in stationary manner, a dispenser head being assembled on said body, said dispenser head being provided with a dispenser orifice, said assembly further comprising a positioner member that co-operates with said nasal dispenser device, said positioner member including at least a first facial bearing zone that, during actuation, co-operates with the forehead or the bridge of the user's nose, said dispenser head being movable axially relative to said body, said positioner member including at least one hollow sleeve in which said dispenser head is inserted in clamping manner, said positioner member including a second facial bearing zone that is adapted to co-operate with the user's top lip.

Advantageously, said positioner member includes two hollow sleeves, each adapted to a respective nostril.

Advantageously, said positioner member includes third bearing zones that are advantageously removable and that are adapted to co-operate with the sides of the face and/or with the ears of the user.

Advantageously, said positioner member includes a support structure that forms a proximal bearing surface that, during actuation, is suitable for receiving at least one, and advantageously two, of the user's fingers.

Advantageously, said support structure forms said at least one hollow sleeve and said second facial bearing zone.

Advantageously, said positioner member includes a connection element that connects said support structure to said first facial bearing zone.

Advantageously, said connection element is adjustable in three dimensions relative to said support structure.

Advantageously, the vertical insertion angle for inserting the dispenser head into the nostril lies in the range 30° to 60°, advantageously in the range 40° to 50°, preferably about 45°.

Advantageously, the horizontal insertion angle for inserting the dispenser head into the nostril lies in the range 0° to 10°, advantageously about 5°.

Advantageously, the insertion depth for inserting the dispenser head into the nostril lies in the range 5 mm to 15 mm, advantageously about 10 mm.

In a first advantageous variant, said reservoir contains only a single dose or only two doses of fluid.

In a second advantageous variant, said reservoir contains a plurality of doses of fluid.

These characteristics and advantages and others appear more clearly from the following detailed description, given by way of non-limiting example, and with reference to the accompanying drawings, in which:

FIG. 1 is a diagrammatic side view in perspective of a nasal dispenser device in a first advantageous embodiment of the invention, in its working position;

FIG. 2 is a diagrammatic front view in perspective of the FIG. 1 device, in its working position;

FIG. 3 is a diagrammatic perspective view showing a way of using the device in FIGS. 1 and 2;

Figure 4:
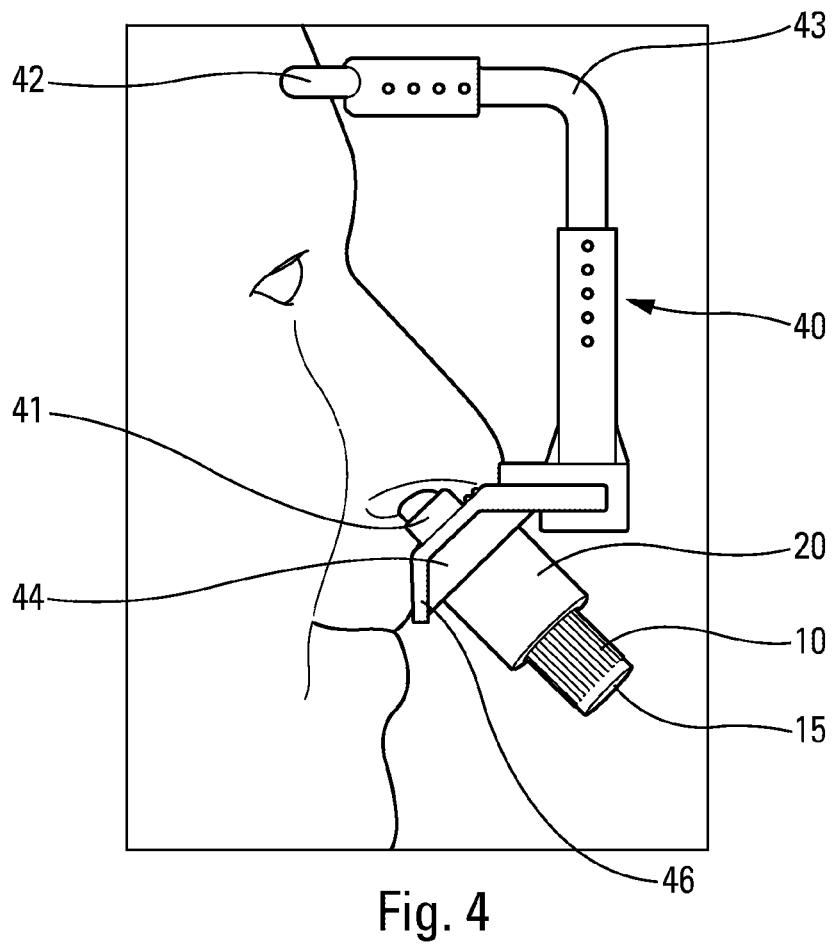
FIG. 4 is a view similar to the view in FIG. 1 of a nasal dispenser device in a second advantageous embodiment of the invention, in its working position.

In the description, the terms "axial" and "radial" are relative to the longitudinal axis X of the device, as shown in FIGS. 1 and 4. The terms "proximal" and "distal" are relative to the dispenser orifice. The terms "horizontal" and "vertical" are relative to a user in the upright position, as shown in FIGS. 1 and 4.

The fluid dispenser device shown in FIGS. 1 to 5 conventionally comprises a body 10 that supports, in stationary manner, a reservoir (not shown) containing fluid. A dispenser head 20 is assembled on said body 10 in axially movable manner relative to said body 10, said dispenser head 20 being provided with a dispenser orifice 21. In a variant, the body 10 may form the reservoir directly, in which variant the dispenser head 20 is mounted directly on the reservoir.

In known manner, said dispenser head 20 includes a proximal bearing surface that, during actuation, is suitable for receiving at least one, and typically two, of the user's fingers. Likewise, the body 10 includes a distal bearing surface 15 that, during actuation, is suitable for receiving one of the user's fingers, and typically the thumb. However, other actuator means, e.g. of the laterally-actuated type, may also be envisaged.

When the device is a multi-dose device, a pump or a metering valve (not shown) is mounted on the body, so as to dispense a dose of fluid on each actuation.

When the device is a single-dose device (the reservoir contains only a single dose) or a two-dose device (the reservoir contains two doses, generally one for each nostril), a piston (not shown) is mounted to slide in the reservoir, said piston being moved, during actuation, by the dispenser head 20 when said dispenser head moves axially relative to the body 10.

In the invention, the device includes a positioner member 40 that co-operates, preferably in removable manner, with said dispenser head 20.

Said positioner member 40 includes at least one hollow sleeve 41 in which said dispenser head 20 is inserted in clamping manner.

Figure 5:
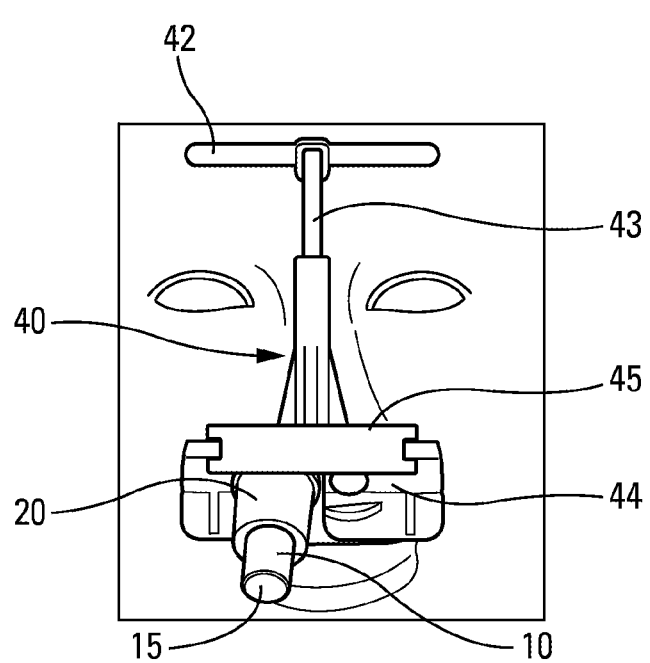
FIG. 5 is a diagrammatic front view in perspective of the FIG. 4 device, in its working position.

Preferably, said positioner member 40 includes two hollow sleeves 41, each adapted to a respective nostril, as can be seen in FIGS. 2 and 5.

The positioner member 40 includes at least a first facial bearing zone that, during actuation, co-operates with the user's face.

The first facial bearing zone 42 is adapted to co-operate with the forehead or the bridge of the nose. As can be seen in the figures, the first facial bearing zone 42 is advantageously of a shape that is rounded.

In the embodiment in FIGS. 1 to 3, the first facial bearing zone 42 is made in the form of a cylinder that bears against the bridge of the nose, between the eyes.

In the embodiment in FIGS. 4 and 5, the first facial bearing zone 42 is made in the form of a horizontal rod that bears against the user's forehead, and that extends sideways on either side of the nose. In a variant, it is possible to envisage two or more bearing zones that are offset sideways on either side of the nose, so as to improve the stability of the assembly in use.

Naturally, any other appropriate shape can be envisaged for the first facial bearing zone 42.

The first facial bearing zone 42 is secured to a connection element 43 that is described more fully below.

A second facial bearing zone 46, adapted to co-operate with the top lip, is also provided.

Figure 6:
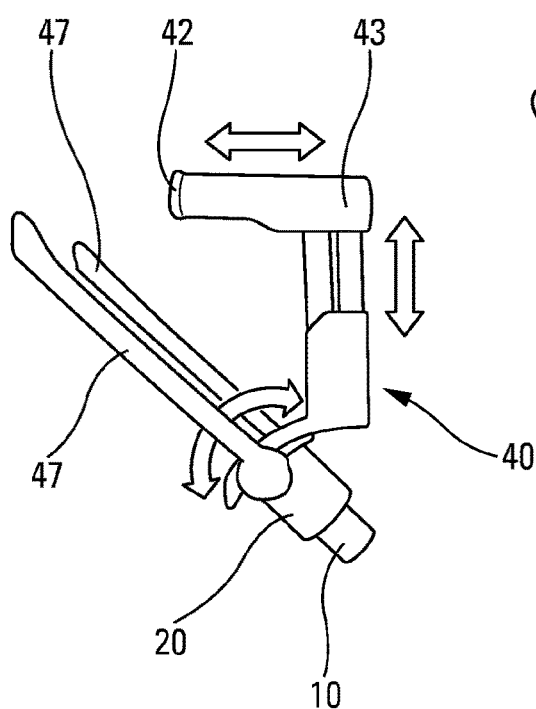
FIGS. 6 to 9 are detail views showing various adjustments of the connection element relative to the support structure.
Figure 7:
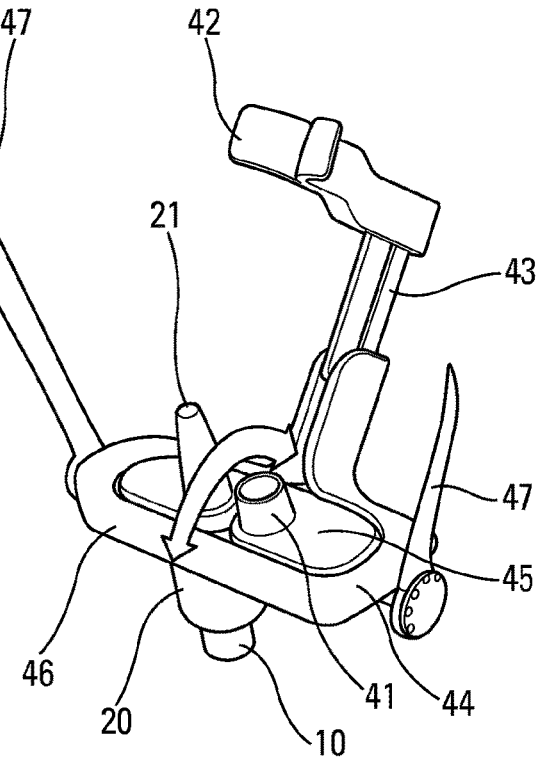
Figure 8:
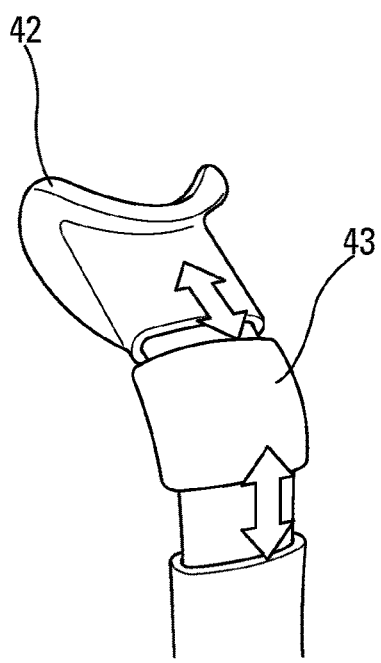
Figure 9:
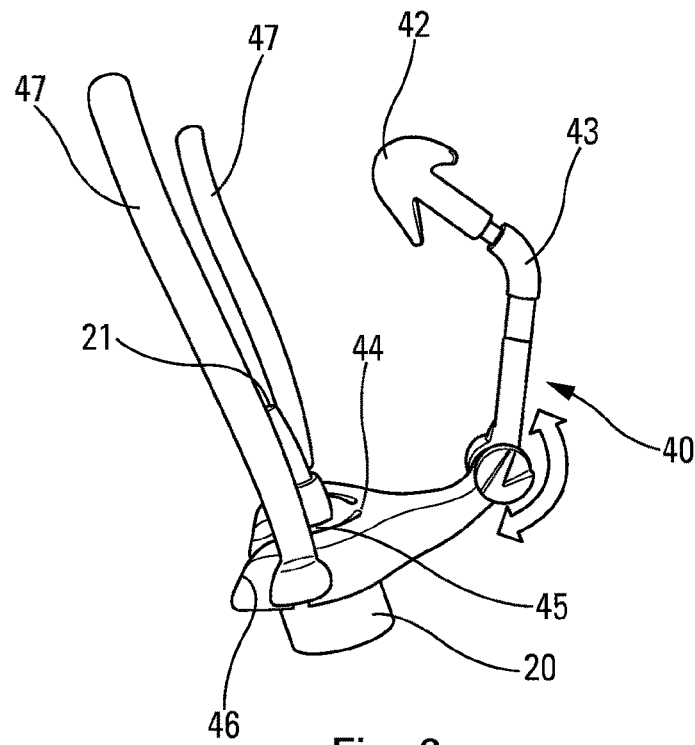

Advantageously, third bearing zones 47 may be provided, e.g. in the form of branches or of rods that are adapted to co-operate with the sides of the face and/or with the ears of the user. The branches 47 can be seen in FIGS. 6, 7, and 9. Such branches 47 may be used to adjust proper positioning of the positioner member 40, and may thus be removable after adjustment so as to avoid hindering the actuation of the device in use.

Advantageously, and as can be seen in FIG. 3, the positioner member 40 includes a support structure 44 that forms a proximal bearing surface 45 suitable for receiving at least one, and advantageously two, of the user's fingers during actuation. The proximal bearing surface 45 thus covers the corresponding bearing surface of the dispenser head 20 so that the actuation movement of the device remains the same, despite the presence of the positioner member 40. In a variant, the device may also be actuated with both hands positioned on the proximal bearing surface 45, on either side of the dispenser head 20.

Advantageously, the support structure 44 also incorporates the hollow sleeve(s) 41, and the second facial bearing zone 46.

The second facial bearing zone 46 is advantageously made by a surface that slopes relative to said proximal bearing surface 45.

Other appropriate shapes are possible for the second facial bearing zone 46.

The connection element 43 makes it possible to connect said support structure 44 to said first facial bearing zone 42. It may be adjustable in three dimensions on said support structure 44, e.g. by means of sliding and/or pivoting portions, as shown diagrammatically and by way of example in FIGS. 6 to 9. This enables accurate adjustment of the positioning of the support structure 44, and thus of the dispenser head 20 to be obtained relative to the connection element 43 and thus relative to the first facial bearing zone 42. Preferably, the horizontal angular positioning of the dispenser head 20 in the nostril, i.e. the angle between the axes X and B in FIG. 2 is constant, so as to guarantee proper orientation of the device during actuation.

Similarly, it is possible to envisage a first facial bearing zone that is adjustable, in particular in height and in width, so as to adapt to the user's morphology.

In the embodiments shown, the connection element 43 is formed by a curved rod, but other appropriate shapes may be envisaged.

The positioner member 40 may orientate the dispenser head 20 in the nostril in substantially predetermined manner.

Thus, the vertical insertion angle for inserting the dispenser head 20 into the nostril, i.e. the angle between the axes X and A in FIG. 1, lies in the range 30° to 60°, advantageously in the range 40° to 50°, preferably about 45°.

Similarly, the horizontal insertion angle for inserting the dispenser head 20 into the nostril, i.e. the angle between the axes X and B in FIG. 2, lies in the range 0° to 10°, advantageously about 5°.

In addition, the insertion depth P for inserting the dispenser head 20 into the nostril lies in the range 5 millimeters (mm) to 15 mm, advantageously about 10 mm.

Figure 10:
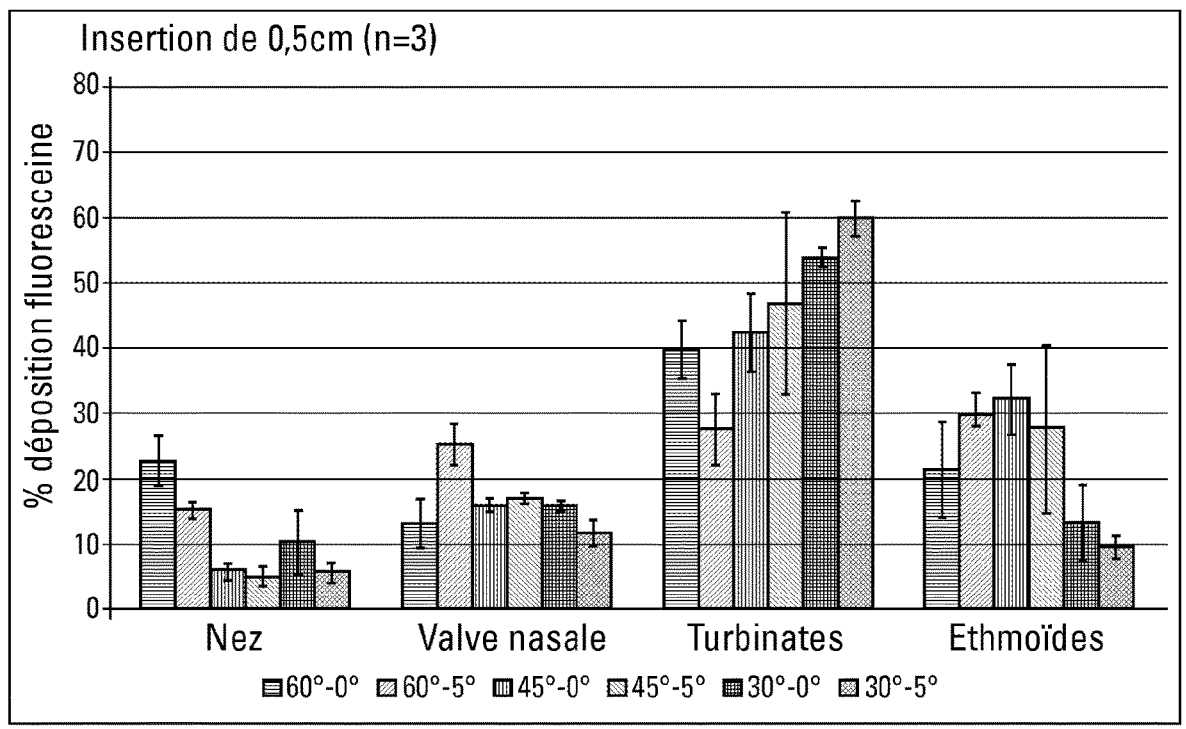
FIGS. 10 and 11 are bar charts showing comparative tests of deposition in the nose, at various angles of insertion, and respectively at two different insertion depths in the nostril.
Figure 11:
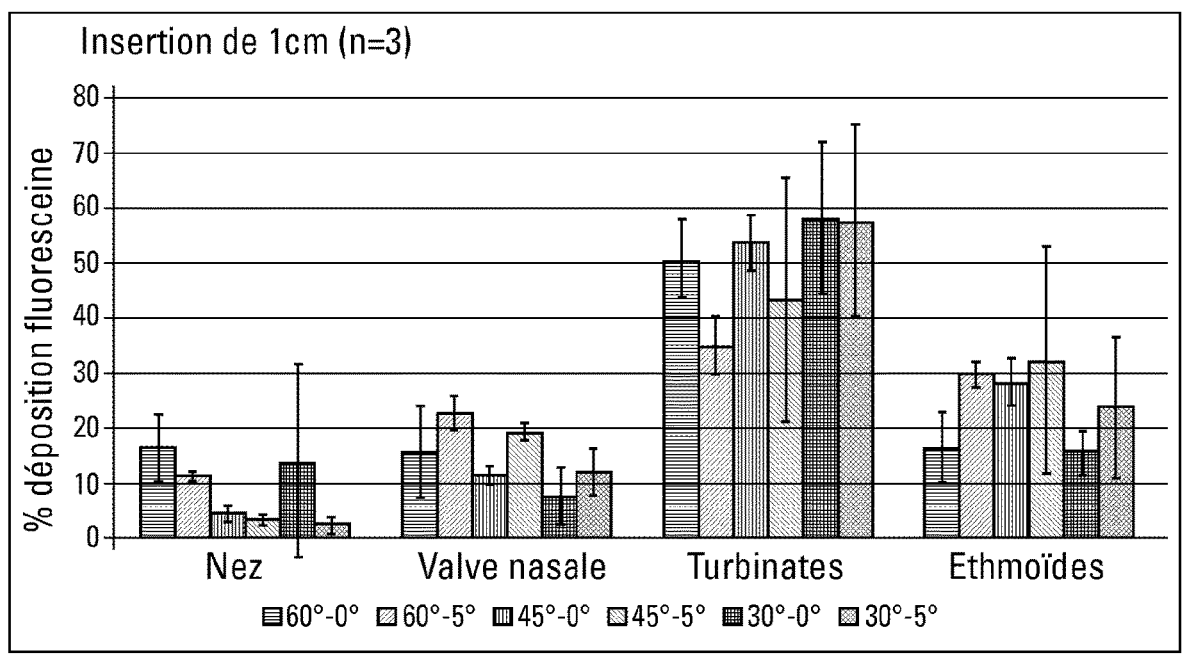

FIGS. 10 and 11 show comparative tests of depositing the fluid in various parts of the nose: the inlet, known herein as the nose; the nasal valve; the turbinates; and the ethmoid sinuses which are the preferred target.

FIG. 10 shows the results at various vertical angles (tests performed at 30°, 45°, and 60°) and various horizontal angles (tests performed at 0° and 5°) for an insertion depth P of 5 mm, and FIG. 11 for an insertion depth P of 10 mm.

It should be observed that the best results at the ethmoid sinuses are achieved with a vertical angle of 45°. When the insertion depth P is 5 mm, a horizontal angle of 0° associated with the vertical angle of 45° is optimum. When the insertion depth P is 10 mm, a horizontal angle of 5° associated with the vertical angle of 45° is optimum.

It should also be observed that at a vertical angle of 45°, a difference exists between a horizontal angle of 0° and a horizontal angle of 5°, but it is not large, and this applies whatever the insertion depth. In contrast, at a vertical angle of 60°, the difference becomes large.

It can be deduced therefrom that the ideal combination corresponds to an insertion depth P of about 10 mm, a vertical angle of about 45°, and a horizontal angle of about 5°.

The present invention is particularly adapted for treatment of neurodegenerative diseases of the Parkinson or Alzheimer type that require medication to be delivered via the nose-brain barrier. Reaching the target zone, in particular the ethmoid sinuses, via the nasal cavity is a simple and non-invasive means of administering a treatment to the brain.

The present invention is described above with reference to various advantageous embodiments, but it is clear that any modification could be applied thereto by a person skilled in the art, without going beyond the ambit of the present invention, as defined by the accompanying claims.

The invention claimed is:

1. A dispenser assembly comprising a nasal fluid dispenser device comprising a body comprising a reservoir containing fluid, a dispenser head assembled on said body, said dispenser head provided with a dispenser orifice, said dispenser assembly further comprising a positioner member that co-operates with said nasal fluid dispenser device, said positioner member comprising a first facial bearing zone that, during actuation of the nasal fluid dispenser device, is configured to co-operate with a forehead or a bridge of the user's nose, wherein said dispenser head is movable axially relative to said body during said actuation, said positioner member including at least one hollow sleeve in which said dispenser head is inserted, said positioner member including a second facial bearing zone that is adapted to co-operate with the user's top lip.

2. An assembly according to claim 1, wherein said positioner member includes two hollow sleeves, each for a respective nostril.

3. An assembly according to claim 1, wherein said positioner member includes third bearing zones that are advantageously removable and that are adapted to co-operate with the sides of the face and/or with the ears of the user.

4. An assembly according to claim 1, wherein said positioner member includes a support structure that forms a proximal bearing surface that, during actuation, is suitable for receiving at least one of the user's fingers.

5. An assembly according to claim 4, wherein said support structure forms said at least one hollow sleeve and said second facial bearing zone.

6. An assembly according to claim 4, wherein said positioner member includes a connection element that connects said support structure to said first facial bearing zone.

7. An assembly according to claim 6, wherein said connection element is adjustable in three dimensions relative to said support structure.

8. An assembly according to claim 1, wherein a vertical insertion angle, relative to a vertical orientation of a user's head in an upright position, for inserting the dispenser head into the nostril lies in the range of 30° to 60°.

9. An assembly according to claim 1, wherein a horizontal insertion angle, relative to an axis orthogonal to a vertical orientation of a user's head in an upright position, for inserting the dispenser head into the nostril lies in the range of 0° to 10°.

10. An assembly according to claim 1, wherein an insertion depth (P) for inserting the dispenser head into the nostril lies in the range of 5 mm to 15 mm.

11. An assembly according to claim 1, wherein said reservoir contains only one or two doses of fluid.

12. An assembly according to claim 1, wherein said reservoir contains a plurality of doses of fluid.

13. The assembly according to claim 1, wherein said positioner member includes a support structure that forms a proximal bearing surface that, during actuation, is suitable for receiving two of the user's fingers.

14. The assembly according to claim 1, wherein a vertical insertion angle, relative to a vertical orientation of a user's head in an upright position, for inserting the dispenser head into the nostril lies in the range of 40° to 50°.

15. The assembly according to claim 1, wherein a vertical insertion angle, relative to a vertical orientation of a user's head in an upright position, for inserting the dispenser head into the nostril is about 45°.

16. The assembly according to claim 1, wherein a horizontal insertion angle, relative to an axis orthogonal to a vertical orientation of a user's head in an upright position, for inserting the dispenser head into the nostril is about 5°.

17. The assembly according to claim 1, wherein an insertion depth for inserting the dispenser head into the nostril is about 10 mm.

* * * * *